(12) United States Patent
Morgan et al.

(10) Patent No.: US 6,261,283 B1
(45) Date of Patent: Jul. 17, 2001

(54) LIQUID VENTING SURGICAL SYSTEM AND CASSETTE

(75) Inventors: Michael D. Morgan, Costa Mesa; Gary P. Sorensen, Lake Forest, both of CA (US)

(73) Assignee: Alcon Universal Ltd., Hunenberg (CH)

( * ) Notice: Subject to any disclaimer, the term of this patent is extended or adjusted under 35 U.S.C. 154(b) by 0 days.

(21) Appl. No.: 09/387,357

(22) Filed: Aug. 31, 1999

(51) Int. Cl.$^7$ ........................................ A61M 1/00
(52) U.S. Cl. .................. 604/540; 604/543; 604/118; 604/93.01; 604/27; 604/28; 604/35
(58) Field of Search ...................... 604/19, 35, 22, 604/902, 540, 542, 43, 45, 118–120, 317, 319, 320, 324, 27, 28, 543, 93.01

(56) References Cited

U.S. PATENT DOCUMENTS

| | | |
|---|---|---|
| D. 264,134 | 4/1982 | Xanthopoulos . |
| 4,052,987 * | 10/1977 | Wuchinich et al. ............... 128/276 |
| 4,140,118 | 2/1979 | Jassawalla . |
| 4,187,057 | 2/1980 | Xanthoupoulos . |
| 4,223,813 | 9/1980 | Garrett et al. . |
| 4,395,258 | 7/1983 | Wang et al. . |
| 4,444,548 | 4/1984 | Andersen et al. . |
| 4,475,904 | 10/1984 | Wang . |
| 4,479,761 | 10/1984 | Bilstad et al. . |
| 4,493,695 | 1/1985 | Cook . |
| 4,526,515 | 7/1985 | DeVries . |
| 4,537,561 | 8/1985 | Xanthoupoulos . |
| 4,626,248 * | 12/1986 | Scheller ........................... 604/319 |
| 4,627,833 | 12/1986 | Cook . |
| 4,713,051 | 12/1987 | Steppe et al. . |
| 4,735,610 | 4/1988 | Akkas et al. . |
| 4,758,220 | 7/1988 | Sundblom et al. . |
| 4,758,238 | 7/1988 | Sundblom et al. . |
| 4,773,897 | 9/1988 | Scheller et al. . |
| 4,798,580 | 1/1989 | DeMeo et al. . |
| 4,832,685 | 5/1989 | Haines . |
| 4,838,865 | 6/1989 | Flank et al. . |
| 4,921,477 | 5/1990 | Davis . |
| 4,935,005 | 6/1990 | Haines . |
| 4,963,131 | 10/1990 | Wortrich . |
| 5,041,096 | 8/1991 | Beuchat et al. . |
| 5,106,366 | 4/1992 | Steppe . |
| 5,125,891 | 6/1992 | Hossain et al. . |
| 5,163,900 | 11/1992 | Wortrich . |
| 5,195,960 | 3/1993 | Hossain et al. . |
| 5,242,404 * | 9/1993 | Conley et al. .................... 604/119 |
| 5,267,956 | 12/1993 | Beuchat . |
| 5,364,342 | 11/1994 | Beuchat et al. . |
| 5,403,277 | 4/1995 | Dodge et al. . |
| 5,424,040 | 6/1995 | Bjornsson . |
| 5,460,490 | 10/1995 | Carr et al. . |
| 5,499,969 * | 3/1996 | Beuchat et al. ..................... 604/30 |
| 5,697,898 * | 12/1997 | Devine ............................... 604/22 |
| 5,704,927 | 1/1998 | Gillette et al. . |
| 5,747,824 | 5/1998 | Jung et al. . |

FOREIGN PATENT DOCUMENTS

| | | |
|---|---|---|
| 0 319 273 | 11/1988 | (EP) . |
| 2176717A | 1/1987 | (GB) . |

\* cited by examiner

*Primary Examiner*—Richard K. Seidel
*Assistant Examiner*—Jennifer Maynard
(74) *Attorney, Agent, or Firm*—Jeffrey S. Schira

(57) ABSTRACT

A surgical system having a cassette with an aspirant collection chamber and an aspiration vent line that draws fluid from the aspirant collection chamber. The pressure within the collection chamber is maintained near ambient so that when the aspiration vent line is open, fluid flows from the collection chamber and into the aspiration line. Such a system does not require a second source of irrigation fluid, minimizes pressure surges into the irrigation fluid line and does not affect the fluidic performance of the aspiration system. In addition, various vent pressures can be achieved by varying the vertical position of the reservoir relative to the aspiration line.

3 Claims, 1 Drawing Sheet

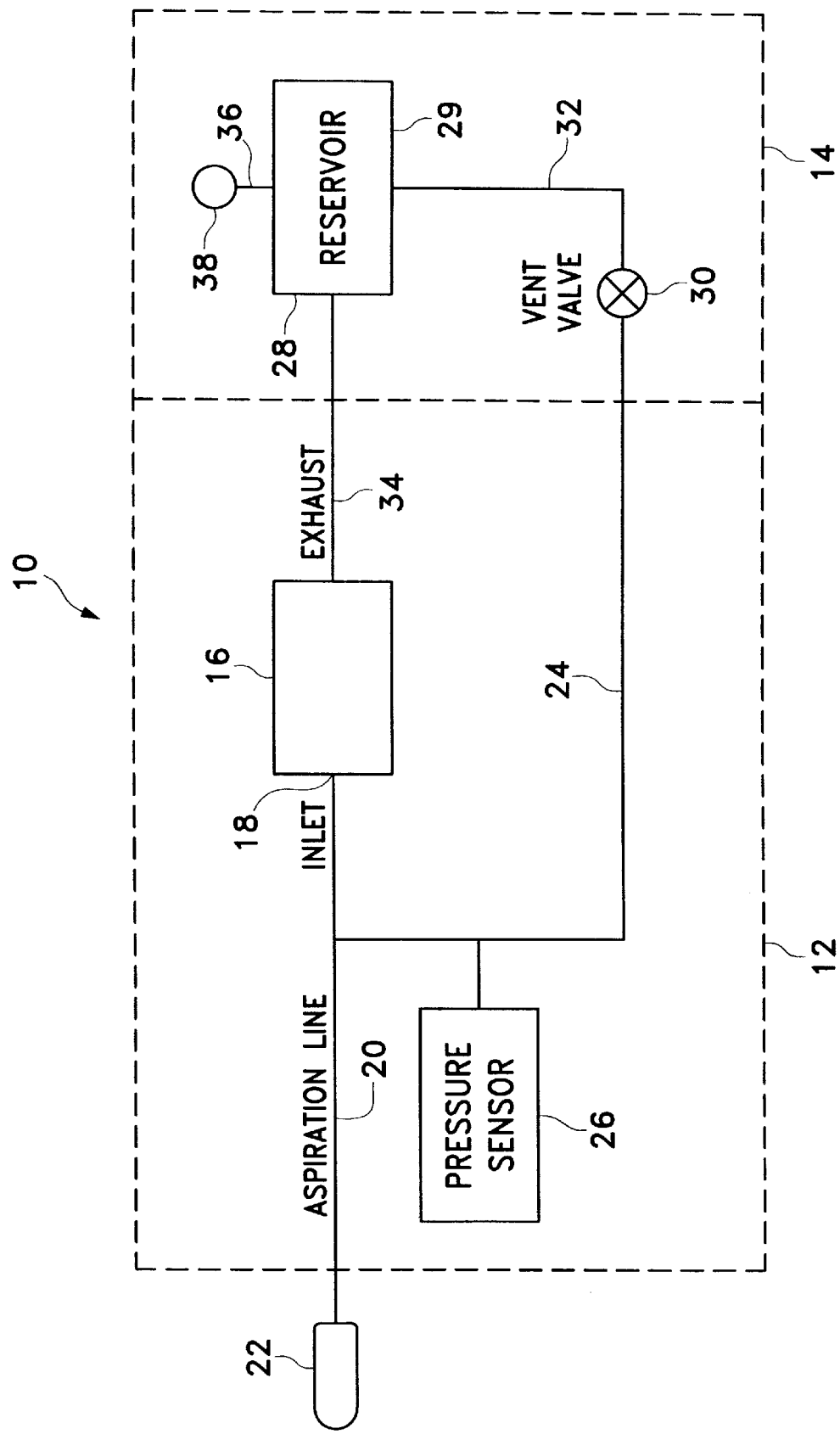

LIQUID VENTING SURGICAL SYSTEM AND CASSETTE

BACKGROUND OF THE INVENTION

This invention relates generally to the field of cataract surgery and more particularly to an aspiration system for a handpiece for practicing the phacoemulsification technique of cataract removal.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; 4,922,902; 4,989,583; 5,154,694 and 5,359,996, the entire contents of which are incorporated herein by reference.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

During surgery, the hollow, resonating tip can become occluded. During occlusion, vacuum can build in the aspiration line downstream of the occlusion. When the occlusion eventually breaks apart, this pent up vacuum is released into the eye which can, depending upon the amount of vacuum, draw a significant amount of fluid from the eye, thereby increasing the risk of anterior chamber collapse. To address this concern, modern surgical console can detect increases in aspiration line vacuum beyond normal operating parameters and therefore predict occlusions. These consoles can then either stop or slow the aspiration pump, or sound an alarm so that the surgeon can take appropriate precautions.

The cassettes used in modern consoles also allow the aspiration line to be vented, either to atmosphere or to a liquid so as to reduce or eliminate vacuum surge upon occlusion break. Prior art air vented cassettes allow ambient air to enter the aspiration line, however, venting air into the aspiration line changes the fluidic performance of the aspiration system. Liquid venting systems allow irrigation fluid to bleed into the aspiration line, thereby reducing any impact on the fluidic performance of the aspiration system. Liquid venting cassettes are more fully described in U.S. Pat. Nos. 4,832,685 and 4,935,005 (Haines) and U.S. Pat. No. 4,713,051 (Steppe, et al.), the entire contents of which being incorporated herein by reference. When higher aspiration vacuums are used, cassettes that vent the aspiration line to the irrigation line can cause high pressure surges in the irrigation line. Other systems provide a separate source of irrigation fluid to vent the aspiration line, requiring the use of two irrigation fluid sources and increasing the cost and complexity of the system.

Therefore, a need continues to exist for a simple surgical system that allows rapid venting of excess aspiration vacuum without introducing pressure variations in the irrigation line or the downstream aspiration line.

BRIEF SUMMARY OF THE INVENTION

The present invention improves upon the prior art by providing a surgical system having a cassette with an aspirant collection chamber and an aspiration vent line that draws fluid from the aspirant collection chamber. The pressure within the collection chamber is maintained near ambient so that when the aspiration vent line is open, fluid flows from the collection chamber and into the aspiration line. Such a system does not require a second source of irrigation fluid, minimizes pressure surges into the irrigation fluid line and does not affect the fluidic performance of the aspiration system. In addition, various vent pressures can be achieved by varying the vertical position of the reservoir relative to the aspiration line.

Accordingly, one objective of the present invention is to provide a surgical system having a aspiration line vent.

Another objective of the present invention is to provide a surgical system having a cassette that allows the aspiration line to be vented of excess vacuum.

Another objective of the present invention is to provide a surgical system having a cassette that vents the aspiration line to an aspirant collection chamber.

Another objective of the present invention is to provide a surgical system that vents the aspiration line without introducing pressure surges in the irrigation line.

Another objective of the present invention is to provide a surgical system that vents the aspiration line without affecting the fluidic performance of the aspiration system.

These and other advantages and objectives of the present invention will become apparent from the detailed description and claims that follow.

BRIEF DESCRIPTION OF THE DRAWINGS

The drawing is a schematic illustration of the system and cassette of the present invention.

DETAILED DESCRIPTION OF THE INVENTION

System 10 of the present invention generally includes surgical console 12 and cassette 14. Console 12 may be any suitably modified commercially available surgical console, such as the SERIES TWENTY THOUSANDS® LEGACY® or ACCURUS® surgical systems available from Alcon Laboratories, Fort Worth, Tex. Cassette 14 may be any suitably modified commercially available surgical cassettes, such as those described in U.S. Pat. Nos. 5,267,956, 5,364,342 and 5,499,969 (Beuchat, et al.) and U.S. Pat. No. 5,899,674 (Jung, et al.), the entire contents of which being incorporated herein by reference. Cassette 14 is held in operative association with console 12 by means well-known in art.

As seen in the figure, console 12 generally contains aspiration pump mechanism 16, which may be any suitable flow or vacuum based pump, such pumps being widely known in the art. For example, pump mechanism 16 may be a peristaltic pump roller head that interacts with a peristaltic pump tube formed by aspiration line 20 and aspiration exhaust line 34. Aspiration line 20 is connected to surgical handpiece 22 on one end and end 18 of aspiration line 20 opposite handpiece 22 interacts with pump mechanism 16 so as to draw fluid through handpiece 22. Aspiration line 20 is intersected between handpiece 22 and 18 by aspiration vent line 24. In fluid communication with aspiration vent line 24 is pressure sensor 26, which may be one of a variety of invasive or non-invasive pressure sensors well-known in the art.

Cassette 14 generally contains fluid reservoir 28. Extending from reservoir 28 at or near bottom 29 is aspiration vent line 32, which fluidly connects to aspiration vent line 24 through vent valve 30. Aspirant or exhaust from pump mechanism 16 is directed into reservoir 28 through aspiration exhaust line 34. Reservoir 28 may also vent to ambient through reservoir vent line 36 which may contain antimicrobial filter 38.

As discussed above, while it is preferred that pump mechanism 16 be a peristaltic roller head and that aspiration line 20 and aspiration exhaust line 34 be formed in one continuous length so as to form a peristaltic pump tube that interacts with pump mechanism 16, one skilled in the art will recognize that aspiration line 20 and aspiration exhaust line 34 may be formed as a separate piece or pieces or may be formed integrally with cassette 14 and that pump mechanisms 16 other than peristaltic pump roller heads may be used, such as linear peristaltic pumps.

In addition, pressure sensor 26 is depicted as being contained within console 12. One skilled in the art will recognize that portions of pressure sensor 26, such as a pressure diaphragm (not shown) may be contained in or on cassette 14 and interact with a force transducer or other means (not shown) contained within console 12.

In use, cassette 14 is installed on or within console 12 and held in operative association with console 12 by means well-known in the art. System 10 is primed initially with clean surgical fluid so that a small amount of fluid fills reservoir 28. During surgery, pump mechanism 16 draws aspirant through handpiece 22 and into reservoir 28. If the vacuum within aspiration line 20 is too high and needs to be vented, vent valve 30 is opened allowing aspirant to be drawn from reservoir 28 at or near bottom 29 (reservoir 28 being at or near ambient) and into aspiration line 20 (which contains a vacuum) through aspiration vent line 24. One skilled in the art will recognize that by varying the vertical position of reservoir 28 relative to aspiration line 20, various vent head pressures may be achieved.

This description is given for purposes of illustration and explanation. It will be apparent to those skilled in the relevant art that changes and modifications may be made to the invention described above without departing from its scope or spirit.

We claim:

1. A surgical system, comprising:
   a) a surgical console containing an aspiration pump mechanism;
   b) an aspiration line fluidly connected on a first end to a handpiece and to the aspiration pump mechanism on a second end so that the aspiration pump mechanism draws fluid through the handpiece;
   c) a cassette containing a fluid reservoir, the cassette being held in operative association with the surgical console;
   d) an aspiration exhaust line fluidly connecting the pump mechanism to the reservoir so that fluid drawn through the handpiece by the pump mechanism flows into the reservoir;
   e) an aspiration vent line extending from the reservoir at or near a bottom of the reservoir, the aspiration vent line fluidly connecting the reservoir to the aspiration line between the handpiece and the pump mechanism; and
   g) a vent valve spaced within the aspiration vent line.

2. The surgical system of claim 1 wherein the cassette further comprises a vent to head pressure determined by the vertical position of the reservoir relative to the aspiration line.

3. A method of venting an aspiration line extending from a hand piece to an aspiration pump mechanism, the method comprising the steps of:
   a) providing a surgical cassette having a fluid reservoir;
   b) fluidly connecting the aspiration line to the fluid reservoir through the pump mechanism;
   c) fluidly connecting the reservoir at or near a bottom of the reservoir to the aspiration line between the handpiece and the aspiration pump mechanism through a vent valve;
   d) opening the vent valve to allow aspirant contained in the reservoir to enter the aspiration line upstream of the aspiration pump mechanism.

* * * * *